(12) United States Patent
McLuckey et al.

(10) Patent No.: US 8,598,517 B2
(45) Date of Patent: *Dec. 3, 2013

(54) METHOD AND APPARATUS FOR ACTIVATION OF CATION TRANSMISSION MODE ION/ION REACTIONS

(75) Inventors: Scott A. McLuckey, West Lafayette, IN (US); Yu Xia, West Lafayette, IN (US); Hongling Han, Lexington, MA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/809,280

(22) PCT Filed: Dec. 17, 2008

(86) PCT No.: PCT/US2008/087099
§ 371 (c)(1),
(2), (4) Date: Sep. 2, 2010

(87) PCT Pub. No.: WO2009/085794
PCT Pub. Date: Dec. 17, 2008

(65) Prior Publication Data
US 2010/0314537 A1    Dec. 16, 2010

Related U.S. Application Data

(60) Provisional application No. 61/008,437, filed on Dec. 20, 2007.

(51) Int. Cl.
*H01J 49/26* (2006.01)
(52) U.S. Cl.
USPC ............ 250/283; 250/281; 250/282; 250/288

(58) Field of Classification Search
USPC ................................. 250/281, 282, 283, 288
See application file for complete search history.

(56) References Cited

U.S. PATENT DOCUMENTS

| 2,939,952 | A | 6/1960 | Paul et al. |
| 5,324,939 | A | 6/1994 | Louris et al. |
| 6,797,949 | B2 | 9/2004 | Hashimoto et al. |
| 7,227,137 | B2 | 6/2007 | Londry et al. |
| 7,232,993 | B1 | 6/2007 | Specht et al. |

(Continued)

FOREIGN PATENT DOCUMENTS

| EP | 1 339 088 A2 | 9/2002 |
| EP | 1 341 205 A2 | 12/2002 |

(Continued)

OTHER PUBLICATIONS

McLuckey et al., "Ion Parking during Ion/Ion Reactions in Electrodynamic Ion Traps", Analytical Chemistry 2002, 74 pp. 336-342.*

(Continued)

*Primary Examiner* — Nicole Ippolito
(74) *Attorney, Agent, or Firm* — Brinks Gilson & Lione

(57) ABSTRACT

A method and apparatus for radial activation of transmission-mode electron transfer ion/ion reactions using a dipolar AC field applied transverse to a transit direction is disclosed. Increases in fragment ion yields and structural information from electron transfer dissociation (ETD) were observed. The method may be used for transmission mode ETD for relatively low charge states of peptides and proteins.

23 Claims, 13 Drawing Sheets

(56) References Cited

U.S. PATENT DOCUMENTS

| | | | |
|---|---|---|---|
| 7,365,319 | B2 | 4/2008 | Hager et al. |
| 7,498,569 | B2 | 3/2009 | Ding |
| 7,608,819 | B2 | 10/2009 | Baba et al. |
| 7,842,917 | B2 * | 11/2010 | McLuckey et al. ............ 250/283 |
| 2005/0221500 | A1 * | 10/2005 | Reid et al. ........................ 436/86 |
| 2006/0192112 | A1 * | 8/2006 | Mordehal .................... 250/290 |
| 2008/0014656 | A1 | 1/2008 | Thomson |
| 2008/0078927 | A1 | 4/2008 | Guna |
| 2008/0135746 | A1 * | 6/2008 | Wildgoose et al. ........... 250/283 |
| 2008/0230691 | A1 | 9/2008 | Hager |
| 2009/0230302 | A1 * | 9/2009 | Hunt et al. ................... 250/282 |
| 2010/0059673 | A1 * | 3/2010 | Makarov et al. ............. 250/283 |

FOREIGN PATENT DOCUMENTS

| | | |
|---|---|---|
| JP | 2003-242926 A | 2/2002 |
| JP | 2003-249190 A | 2/2002 |
| WO | WO 2005/074004 A2 | 8/2005 |
| WO | WO 2006/042187 A2 | 4/2006 |
| WO | WO 2006/129068 A2 | 12/2006 |
| WO | WO 2008/069962 A2 | 6/2008 |

OTHER PUBLICATIONS

Xia, Y. et al., "Activation of Intact Electron-Transfer Products of Polypeptides and Proteins in Cation Transmission Mode Ion/Ion Reactions," Anal. Chem., 2008, 80, pp. 1111-1117.

Written Opinion of the International Searching Authority from the International Search Report from PCT application No. PCT/US2008/087099 dated Jul. 20, 2009, 4 pages.

International Search Report for International Application No. PCT/US2008/087099, dated Jul. 20, 2009, 3 pages.

Office Action from related Japanese Patent Application No. 2009-539335 mailed Jul. 13, 2012.

* cited by examiner

METHOD AND APPARATUS FOR ACTIVATION OF CATION TRANSMISSION MODE ION/ION REACTIONS

This application is the national stage of PCT/US08/87099, filed on Dec. 17, 2008, which claims the benefit of U.S. provisional application 61/008,437, filed on Dec. 20, 2007.

TECHNICAL FIELD

This application relates to an apparatus and method of analyzing molecules and, in particular, biomolecules.

BACKGROUND

The characterization of a gas-phase ion primary structure may rely on information that can be obtained from the dissociation thereof. In the context of proteomics, protein identification and characterization may be conducted via tandem mass spectrometry using one or more gas-phase ion dissociation techniques. A commonly used method for activating polypeptide or protein ions is collision-induced dissociation (CID), which involves energetic collisions between ions and inert neutral bath gas atoms or molecules.

CID may be implemented with commercially available tandem mass spectrometers subject to a variety of operating conditions. These conditions may range from the slow activation (ms to s) low-collision-energy regime (<100 eV), of an ion trapping instrument (e.g., electrodynamic ion trap or penning trap) to the fast activation (μs), high collision energy regime (keV), in a beam-type instrument (e.g., a sector or time-of-flight/time-of-flight instrument).

Although the large differences in energies and time-scales associated with the various CID conditions can give rise to significant differences in the relative contributions of the competing peptide ion dissociation channels, structurally informative amide bond cleavages are generally observed, giving rise to b- and y-type ions.

Other than collision with inert gas species, methods using collision with surfaces, termed as surface-induced dissociation have been developed and applied to peptide dissociation studies. Photo-dissociation techniques, including infrared multi-photon dissociation (IRMPD), blackbody infrared dissociation (BIRD) and single-photon UV-photo-dissociation also show utility in providing structural information, which in some cases can complement that derived from other dissociation methods.

In addition to the techniques described above, the informative dissociation of multiply charged peptide and protein cations arising from the capture of low energy electrons, a phenomenon referred to as electron capture dissociation (ECD) may be employed. In ECD, the N—Cα bonds of the peptide backbone are cleaved, giving rise to sequence informative c- and z-type complementary ions. Compared to CID, ECD exhibits less sequence dependence on the cleavage sites and preservation of the post-translational modifications (PTMs), allowing characterization of modified protein ions.

The ion/ion reaction analogue to ECD is electron transfer dissociation (ETD), where the electron is transferred (ET) from an anion to a multiply-charged peptide or protein cation. ETD has been implemented on electrodynamic ion traps and it has been suggested that the dissociation due to electron transfer is similar to that observed in ECD. Accompanying dissociation products caused by electron transfer during the positive and negative ion encounters are contributions of varying abundance from electron transfer without subsequent dissociation (ET no D) and proton transfer (PT). The degree of competition from PT appears to be related to the characteristics of the anion reagent and the cation itself. Proton transfer can be minimized by the selection of the anionic reagent but no reagent appears to show exclusive electron transfer. The relative abundance of ET no D products has been observed to be strongly affected by the charge state of a peptide ion (e.g., much higher ET no D for lower charge states), as well as the identity of the protonated sites.

Elevated bath gas temperatures have been used in electron transfer ion/ion reactions. However, an improvement of ETD yields relative to room temperature ETD experiments is not consistently observed.

FIG. 1 shows four ways to effect ion/ion electron transfer dissociation reactions within a linear ion trap (LIT), where both polarity ions can be produced and injected into the LIT in an axial direction. One method involves the storage of neither ion polarity and relies on reactions taking place between the ions of opposite polarity as they are continuously admitted into the LIT (Method I). The likelihood for ion/ion reactions in this mode is expected to be the lowest of the four approaches because the relative velocities of the ions are the highest. Methods II and III involve storing one ion polarity while ions of the other polarity are continuously admitted into the LIT. Method IV employs mutual storage of oppositely charged ions, which is expected to provide the lowest relative velocities of the four approaches. The latter method requires the application of radio frequency (RF) voltages to the containment lenses of the LIT or the application of unbalanced RF to the quadrupole array.

Methods II and III of transmission mode electron transfer ion/ion reactions are taught in U.S. patent application Ser. No. 11/998,306 filed on Nov. 29, 2007, and which is incorporated herein by reference. (In the reference application, the corresponding methods are Methods I and II.)

Ion trap collisional activation of the ET no D products in a 3-D and a linear ion trap (LIT) appears to result in the formation of c- and z-type of ions, which tend to be complementary to those formed directly from ETD. This method has been demonstrated to be effective both in improving ETD yields and in increasing the extent of structural information from ETD with minimal contribution from dissociation of PT products that may also be present.

Beam-type post-ion/ion reaction collisional activation has been performed on a triple quadrupole/linear ion trap (LIT) system, where the ion/ion products, including the surviving precursor ions, are accelerated axially from a second LIT, in the presence of roughly 1 mTorr of nitrogen where the ion/ion reaction occurs in an adjacent first LIT for subsequent mass analysis. By choosing an appropriate acceleration potential, a significant increase in ETD yields can be achieved, although the contribution from the CID of precursor ions and other product ions does not appear to have been eliminated.

These methods for converting ET no D products into ETD products are based on a mutual trapping ion/ion reaction configuration, such as shown in method IV, where positive and negative ions are stored simultaneously in an overlapping space.

SUMMARY

A method of analyzing molecules is disclosed, the method including the steps of: providing a ion trapping volume; injecting a first population of ions into the ion trapping volume so that the first population is stored in the trapping volume; injecting a second population of ions into the ion trapping volume such that at least a partial physical overlap of the first and the second ion populations occurs; producing ionic products by applying an AC electric field to the ion trap; and, performing mass spectrometry on ionic products ejected from the ion trap.

In an aspect, a method of analyzing molecules is disclosed, the method including the steps of: operating a first source of ions; selecting first ions by using a mass filter and injecting the selected first ions into a volume acting as a linear ion trap (LIT), the ion trap being configured to store the first ions; operating a second source of ions; selecting second ions by using the mass filter and injecting the selected second ions into the LIT along an axis thereof; producing ionic products using an AC electric field transverse to the axis of the LIT; and, mass analyzing the ionic products.

In yet another aspect, an apparatus for analyzing molecules includes a linear ion trap (LIT), where the LIT is configured to: accept and store a first population of ions; and, accept and transmit a second population of ions. The apparatus further includes a signal generator configured to apply a dipolar AC voltage to structures of the LIT so as to create an electric field transverse to a LIT axial direction; and a mass analyzer.

DETAILED DESCRIPTION

Exemplary embodiments may be better understood with reference to the drawings, but these embodiments are not intended to be of a limiting nature. In the following description, numerous specific details are set forth in order to provide a thorough understanding of the present invention which, however, may be practiced without some or all of these specific details. In other instances, well known process operations have not been described in detail in order not to unnecessarily obscure the description.

Figure 1:
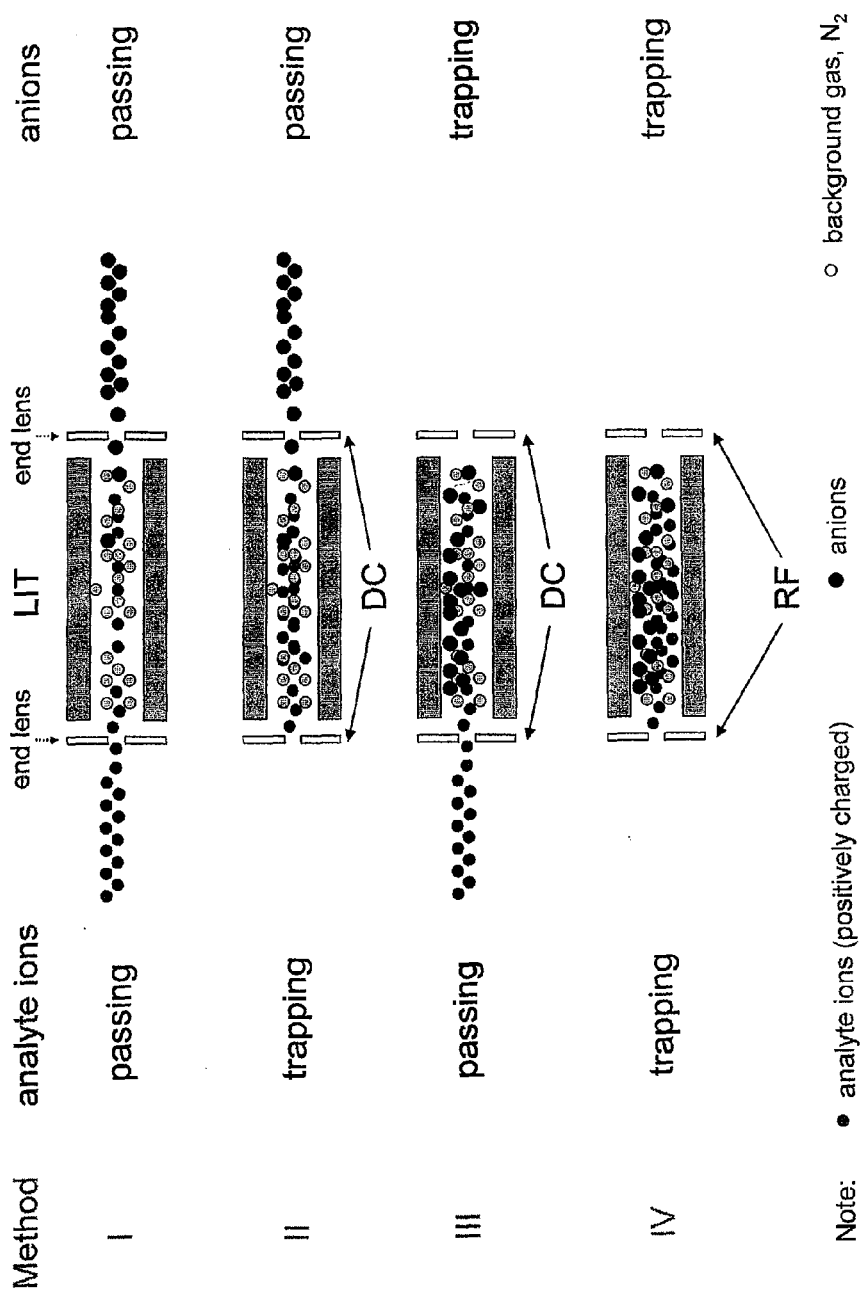
FIG. 1 schematically illustrates four methods for effecting ion/ion electron transfer dissociation reactions in a linear ion trap (LIT): (I) passage of both polarity ions, (II) positive ion storage/negative ion transmission, (III) positive ion transmission/negative ion storage, and (IV) mutual storage of both polarity ions (Prior art)
Figure 2:
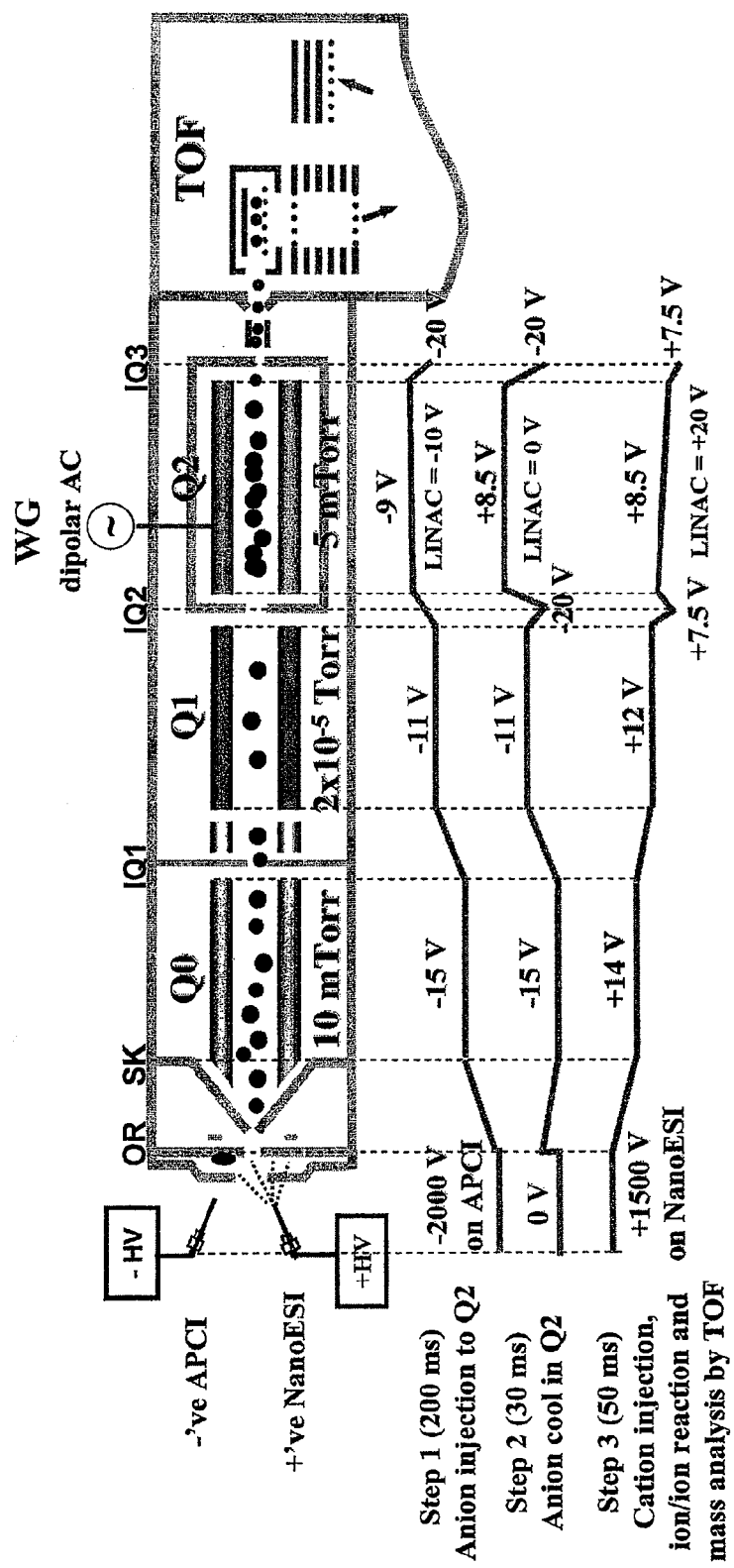
FIG. 2 is a schematic representation of a quadrupole time-of-flight tandem mass spectrometer (QSTAR XL) equipped with a pulsed dual nanoESI/APCI source; the plots below the schematic show the typical potential along the apparatus axis at different steps for positive ion transmission mode ion/ion electron transfer reaction experiments; the voltage levels are not drawn to scale, but the voltage values themselves are indicated.

The apparatus used for the experimental examples herein is a modified commercial quadrupole/time-of-flight (QqTOF) tandem mass spectrometer (QSTAR XL, Applied Biosystems/MDS SCIEX, Concord, ON, Canada), as shown schematically in FIG. 2. The QSTAR apparatus includes three quadrupole arrays: an ion guide Q0, a mass filter Q1, an ion trapping collision cell Q2 (LIT) with a LINAC function, and a reflectron time-of-flight (TOF) analyzer. LINAC refers to the imposition of an axial electric field along the length axis of the Q2 rods during a step in the method, so as to move ions efficiently through the collision cell. The magnitude and the direction of the axial electric field (LINAC) can be adjusted to optimize ion transfer conditions. A dipolar AC voltage may be applied to a pair of axially symmetric rods of the Q2 quadrupole array to effect collisional activation of ions in the radial dimension of Q2.

The operating parameters of the of the QqTOF device, including lens voltages, quadrupole rod offsets, operating pressures, and the and the amplitude and polarity of the LINAC fields are adjusted to optimize transmission mode ETD performance. The experimental sequence was controlled by a research version of MDS SCIEX software, Daetalyst.

The quadrupole time-of-flight apparatus used in these examples has an orifice/skimmer atmospheric pressure/vacuum interface (OR/SK), a high pressure quadrupole ion guide (Q0, 10 mTorr), a quadrupole mass filter (Q1, $2\times10^{-5}$ Torr), and a quadrupole collision/reaction cell (Q2, 5 mTorr).

The commercial apparatus is augmented by an AC voltage generator, which may be a electrical signal generator (WG), such as an Agilent 33220A waveform generator (Agilent, Santa Clara, Calif.), coupled to an opposing pair of rods in the collision cell (Q2) so as to apply a dipolar AC voltage transverse to the axis of the collision cell (Q2). The term "AC" voltage is used rather than "RF" so as to differentiate this voltage from other alternating current "RF" voltages which are a known aspect of the operation of a quadrupole mass spectrometer.

The DC fields of the LINAC may be formed by applying a voltage differential between the input (IQ2) and output lenses (IQ3) of the collision cell (Q2), or by lengthwise segmenting the quadrupole rods of the collision cell (Q2) so as to form short, isolated rod sections at the input and output ends of the cell, to which the differential DC voltage may be applied.

Cationic peptide electron transfer products that do not fragment spontaneously (e.g., ET with no D products) may exposed to ion trap collisional activation immediately upon formation while passing through a collision cell (Q2), where electron transfer reagent anions have been stored.

In an aspect, radial ion acceleration, oriented normal to the axial ion flow, may be imposed by applying a dipolar AC voltage to a pair of axially symmetric opposing rods of the Q2 quadrupole array at a frequency corresponding a resonance frequency of the ET with no D (ET no D) product. Collisional cooling of the cations by the neutral gas present in present in Q2 may result in overlap of the positive and negative ions to permit ion/ion reactions and may also give rise to relatively long residence times for ions in Q2, which may lead to fragmentation of ions by the radial excitation during the axial transmission along the length of the collision cell (Q2).

In a first set experimental examples, the materials used were Myoglobin (horse heart), ubiquitin (bovine), azobenzene, and TPCK-treated trypsin, purchased from Sigma-Aldrich (St. Louis, Mo.). A phosphorylated peptide with a single letter sequence of DLDVPIPGRFDRRVpSVAAE was provided by Prof. W. A. Tao of the Biochemistry Department at Purdue University. Methanol and glacial acetic acid were obtained from Mallinckrodt (Phillipsburg, N.J.). Trifluoroacetic acid was purchased from Pierce (Rockford, Ill.). All samples were used without further purification.

Tryptic digestion was performed on myoglobin (1 mg) and followed by reverse-phase high-performance liquid chromatography (HPLC) separation. One of the resulting tryptic peptides with a single letter sequence of HGTVVLTVLGGILK was used as a model peptide to evaluate electron transfer ion/ion reactions. The peptides and proteins were dissolved to 10 µM in 50/49/1 (v/v/v) methanol/water/acetic acid solutions. The examples of materials, operating conditions of the equipment, equipment configurations, and the like, described herein are by way of example, and are not meant to suggest that the method and apparatus is limited to those materials named, the operating conditions, the equipment configurations, or the equivalents thereof.

An experimental pulsed dual-source ionization device, fabricated in our laboratory, was coupled directly to the nanospray interface of the QSTAR apparatus, and included a nano-electrospray (nanoESI) emitter for the formation of positive peptide ions ($[M+nH]^{n+}$), and an atmospheric pressure chemical ionization (APCI) needle for the formation of radical anions from the electron transfer reagent (azobenzene, in this example).

The pressure in Q2 was approximately 5 mTorr, with nitrogen as a bath gas. Cation transmission-mode electron transfer ion/ion reactions were caused to occur in Q2.

The analysis method includes the steps of: (1) anion injection into Q2 with the Q1 quadrupole operating in a mass-resolving mode to isolate the reagent ions of interest; (2) anion cooling in Q2; and, (3) cation injection into Q2 with the Q1 quadrupole operating in a mass-resolving mode to isolate analyte ions of interest, followed by ion/ion reactions in Q2 and (4) mass analysis by a reflectron-type time-of-flight (TOF) analyzer.

Shown below the simplified representation of the experimental apparatus in FIG. 2 are curves indicating the typical voltage potentials values applied to the relevant ion-optical elements of the system. The voltage scale is not shown; however, the DC voltage profile along the length of the experimental apparatus is shown with numerical values, for each of the first three steps of the method.

The DC potential difference between Q2 and Q0 sets the axial collision energy (CE=(Q0−Q2) z) of ions, where z represents the numerical value of units of charge of the ions. Q2 was normally set 4-6 V more attractive (that is, more negative than) than Q0 for the cation injection step (Step 3), so as to minimize fragmentation caused by axial activation and also to achieve efficient ion/ion reactions. Higher CE values may also be used to evaluate the effect of axial kinetic energy on the dissociation behavior of electron transfer ion/ion reactions.

High potentials are applied when the ionization sources were pulsed on (+1.5 kV for nano-ESI and −2.0 kV for APCI) during the corresponding ion injection periods. The TOF analyzer typically provided a mass resolution of 6000-8000 and mass accuracy of ~50 ppm (using an external calibration). The spectra shown herein are averages of 50-200 individual TOF scans.

Doubly-protonated ions of a tryptic peptide comprised of 14 amino acid residues (HGIVVLTALGGILK) were used to evaluate the effectiveness of ETD in cation transmission-mode ion/ion reactions. FIG. 3a shows data collected for positive-ion transmission-mode electron transfer ion/ion reactions, where $[M+2H]^{2+}$ ions of the peptide are isolated and reacted with radical anions (m/z=182) derived from azobenzene. The ion/ion reaction time of the cation transmission mode may be considered to be the residence time of a cation in Q2, which is estimated to be about 1-5 ms under the experimental conditions described. The potential difference between Q2 and Q0 was 4 V, resulting in a precursor cation kinetic energy of about 8 eV. Under this condition, the fragmentation is believed to be nearly all due to electron transfer dissociation (ETD), with little fragmentation due to collisional activation. Four sequence ions due to ETD were observed ($z_{11}$-$z_{13}$ and $c_{13}$), and all of the observed ions are believed to arise from cleavages close to the termini of the peptide.

The limited extent of ETD may result from fragment ions being held together by non-covalent intra-molecular interactions. That is, ETD may have actually taken place but the dissociation products may not have separated, and the resulting complex appears as intact electron transfer products. This phenomenon may be minimized by the disruption of pre-existing non-covalent interactions prior to the electron transfer reaction or to destroying the non-covalent interactions after the ion/ion reactions. Precursor ion activation to disrupt non-covalent intra-molecular interactions may be performed in the source region and in Q2, while product activation may be performed in Q2.

An attempt was made to accelerate the precursor ions in the source region by setting a large potential difference between the orifice (OR) and the skimmer (SK). When the orifice/skimmer potential difference exceeded about 100 V, fragment ions appeared, which are appear to be mostly b- and y-type ions, which may be due to CID in the source region, indicating that the parent ions may have been vibrationally activated under such a condition.

The surviving 2+ charge state ions of the peptide were isolated in Q1 and injected into Q2. The resulting electron transfer ion/ion reaction data, appeared to be the same as that of FIG. 3a, showing no apparent evidence of an increase either in the abundance or diversity of c- and z-type ions from ETD (data not shown). However, this result may be due to relatively rapid cooling of the precursor ions prior to the ion/ion reaction, most probably in Q0. Q0 is about 20 cm long and is operated with about 10 mTorr pressure of a nitrogen bath gas. Ions entering Q0 may be quickly cooled down and focused in the center.

An alternative to in-source activation may be collisional activation by axial acceleration of ions from Q0 to Q2, an approach which has been used for collisional activation in a QqTOF apparatus. FIG. 3b shows the transmission-mode electron transfer ion/ion reaction data of the 2+ precursor ions acquired with an axial acceleration of 52 eV (e.g., 2+ ions exposed to a LINAC acceleration potential of 26 V). Abundant a-, b- and y-type ions due to CID are observed, together with some low abundance c- and z-type ions, which appear to be the same c- and z-type ions as those that that were observed in FIG. 3a.

The data in FIG. 3b suggest that the CID rate of the 2+ precursor ions may be greater than that of the ion/ion reaction under the conditions used in this example. The ion/ion reaction rate appears to be inversely related to the relative velocity of the oppositely charged ion pairs. Therefore, axial acceleration of the precursor ions into Q2 may be expected to reduce the ion/ion reaction rate. Furthermore, the ion/ion reaction time for the cations may be considered to be the residence time of the ions in Q2, which is inversely related to the kinetic energy of the ions. These two factors (reaction rate and time) combine to mitigate formation of ion/ion reaction products. It may be possible that the population of precursor ions that survive collisional activation and are cooled in Q2 contribute substantially to the ETD products that are detected in the experiment leading to the results shown in FIG. 3b.

The pressure of Q2 may also play a role in affecting the overall ion/ion reaction rate through the ion transmission time and spatial overlap of the two ion polarities. The influence of pressure was assessed by varying the Q2 pressure from about 1 to about 10 mTorr at differing precursor-ion kinetic energies. The experimental data indicate that for the kinetic energy ranges investigated, the reaction rate was minimal below about 4 mTorr and increased rapidly at about 5 mTorr. At pressures greater than 5 mTorr, relatively little further increase in precursor-to-product ion conversion was observed. To maintain a relatively high ion/ion reaction rate, the Q2 pressure was held at about 5 mTorr in the subsequent experiments described.

The kinetic energy of the precursor ions admitted into Q2 was also minimized (4-6 V potential difference between Q0 and Q2) to minimize CID. The experimental results described above suggest that pre-activation of the precursor peptide ions may not be an effective means for improving ETD product ion yields, with the present experiment arrangement.

In the present example, in order to achieve radial activation for ET no D products using the transmission mode in Q2, a dipolar AC voltage was applied to a pair of Q2 quadrupole rods with an AC frequency selected to be a resonant frequency of the ions of interest. The charge-reduced ion population was believed to be comprised of both proton transfer products ($[M+H]^+$) and the ET no D products ($[M+2H]^+$) due to the competition of proton transfer and electron transfer processes during ion/ion reactions.

Collisional activation of the intact electron transfer product (ET no D) ions may give rise to the c- and z-ions characteristic of ETD, while collisional activation of the protonated species may fragment to b- and y-ions. The dissociation of electron transfer products may occur at lower AC voltage excitation amplitudes than for protonated species. By adjusting the operating conditions, ET no D products may be fragmented while minimizing the dissociation of the proton transfer products.

Figure 3:
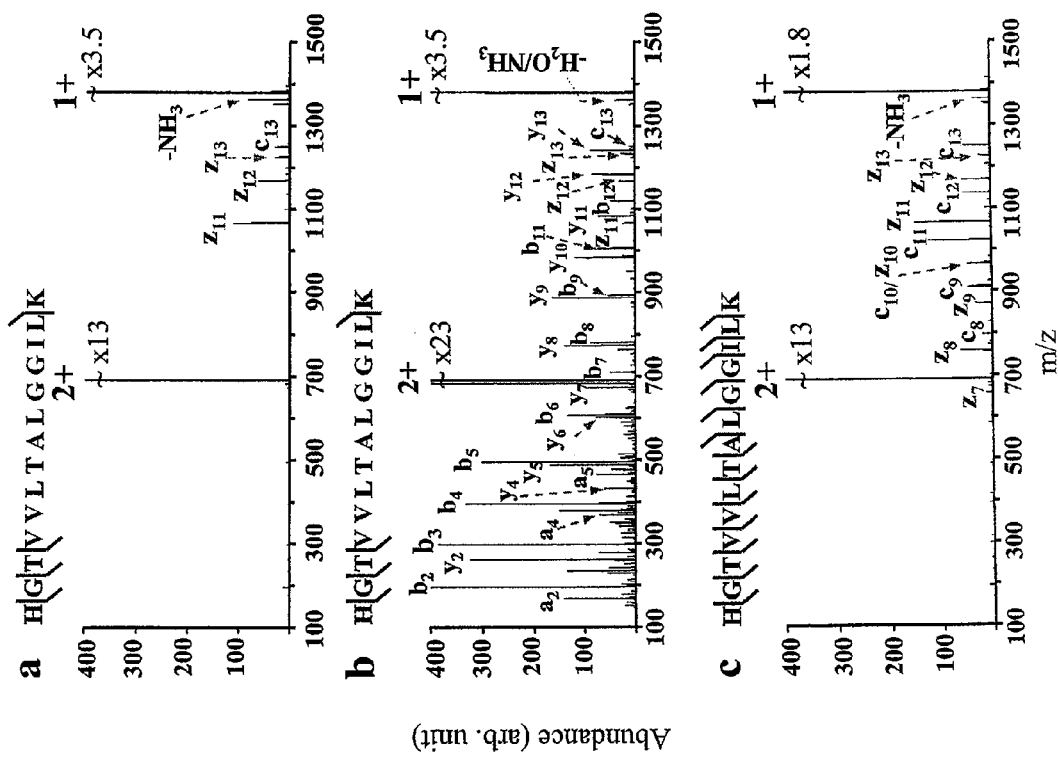
FIG. 3 illustrates spectra derived from cation transmission mode ion/ion reactions between doubly-protonated tryptic peptide (HGIVVLTALGGILK) and azobenzene anions in Q2 with (a) CE=8 eV, no radial activation; (b) CE=52 eV, no radial activation; and, (c) CE=8 eV, radial activation of 1+ charge state of peptide ions by applying a dipolar AC voltage to Q2 (56.47 kHz, 2.3 $V_{p-p}$; the observed ETD cleavage sites are indicated above each spectrum.
Figure 4:
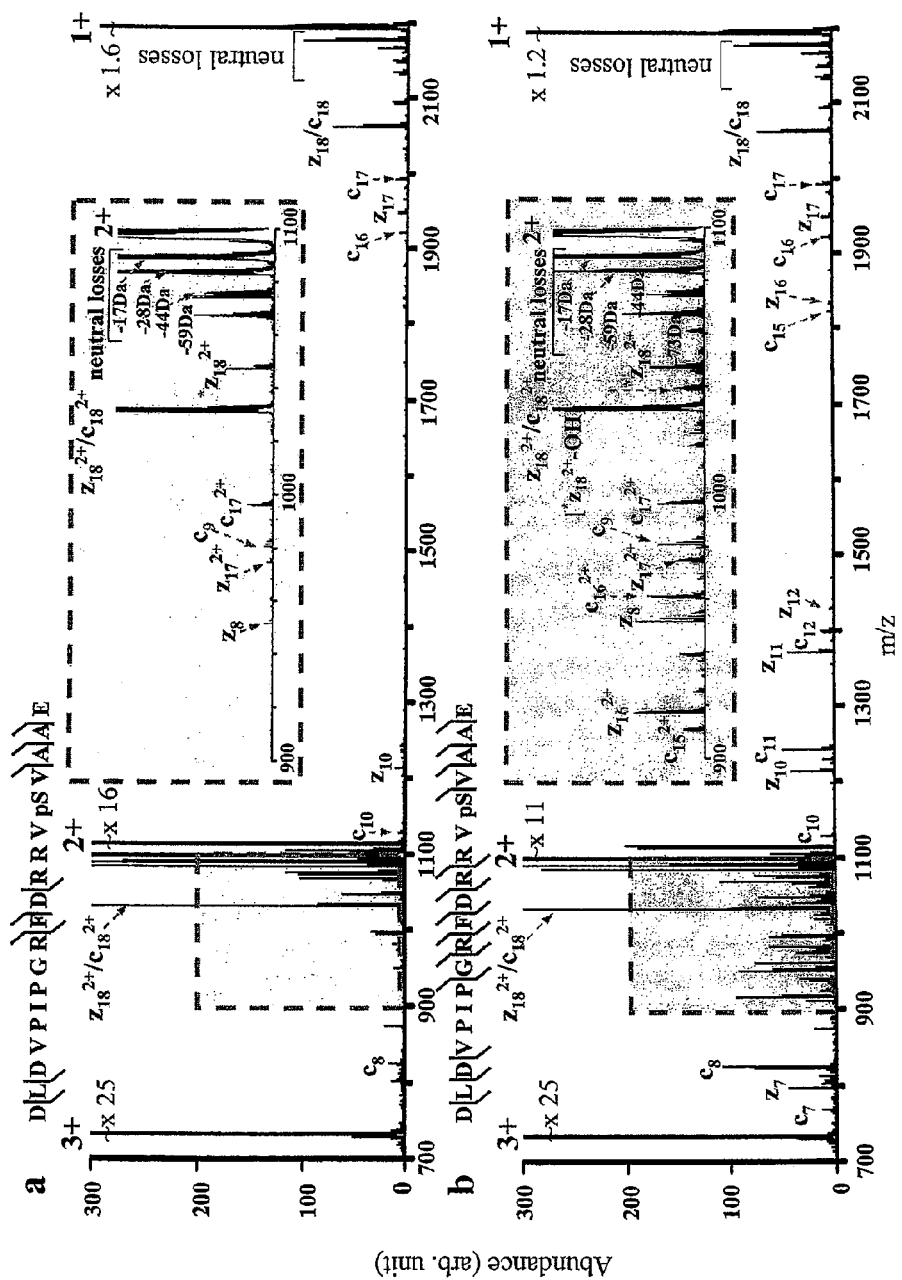
FIG. 4 illustrates the spectra derived from cation transmission mode ion/ion reactions between triply-protonated phosphopeptide (DLDVPIPGRFDRRVpSVAAE) and azobenzene radical anions in Q2 with (a) no radial activation; and, (b) radial activation of 2+ charge state of peptide ions by applying a dipolar AC voltage to Q2 (68.93 kHz, 900 mV$_p$), $z_n$ ions denotes the $O_2$ adducts of the z ions.
Figure 5:
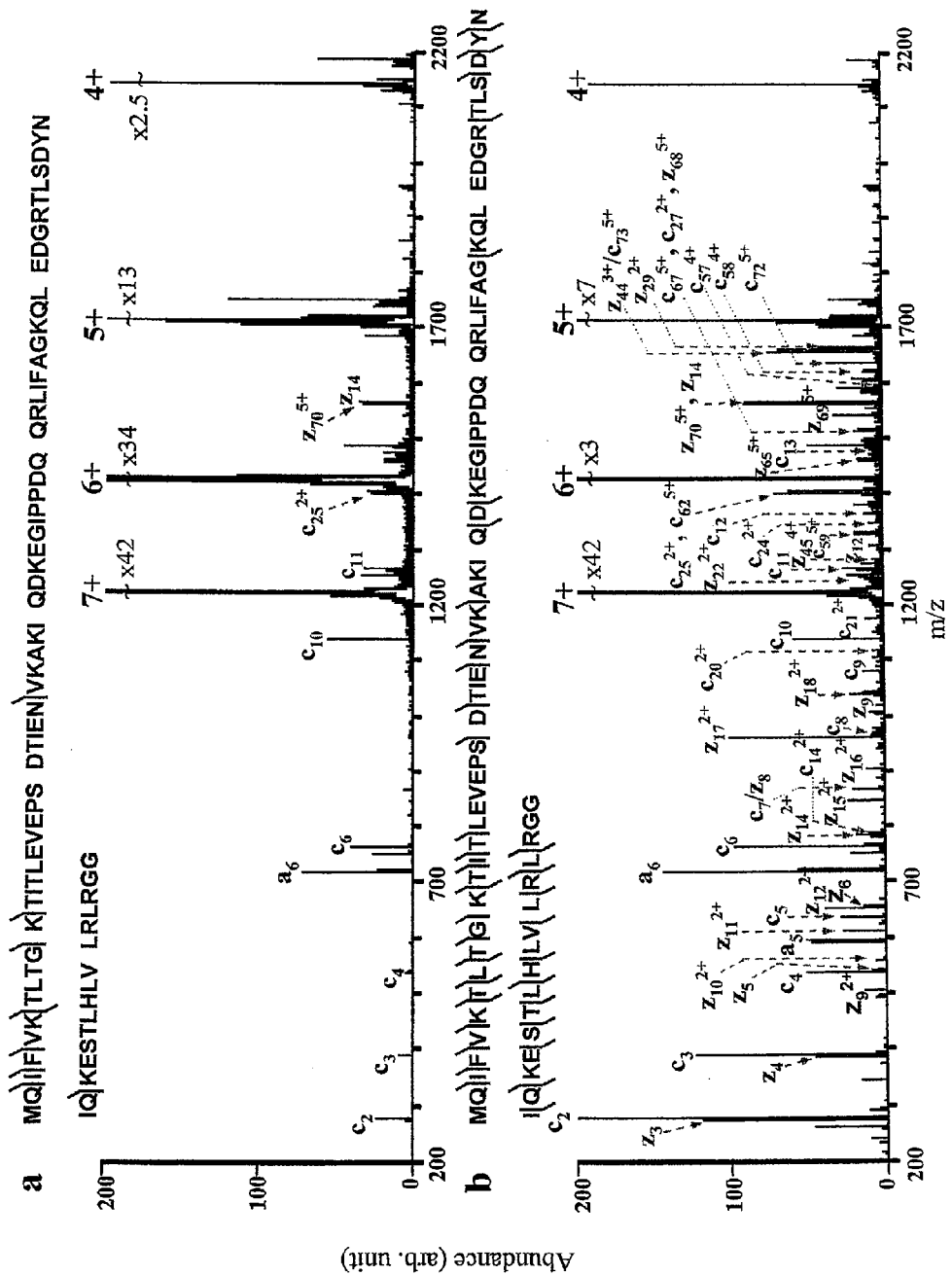
FIG. 5 illustrates the spectra derived from cation transmission mode ion/ion reactions between 7+ charge state of ubiquitin ions and azobenzene anions in Q2 with (a) no radial activation; and, (b) radial activation of the 6+ charge state of ubiquitin ions by applying a dipolar AC voltage to Q2 (52.06 kHz, 500 mV$_{p-p}$)

FIG. 3c shows the ion/ion reaction data resulting from transmission of the doubly-protonated tryptic peptide with an 8 eV CE into Q2, while applying an AC voltage (56.7 kHz, $2.3 V_{p-p}$) to a pair of axially-symmetric rods of the Q2 quadrupole array collision cell, the AC frequency being equal to the resonance frequency of a charge reduced (+1) species of the precursor ions. When compared to FIGS. 3a and 3b, the extent of informative ETD products is significantly increased in FIG. 3c. Thirteen ETD sequence ions are observed including $z_{7-13}$ and $c_{8-13}$, with little contribution from b- and y-type of ions. In addition, the ETD yield (% ETD), defined as the percentage of ETD product types with respect to all the ion/ion products types (surviving precursor ion signals excluded), is improved from 17% in FIG. 3a to 52% in FIG. 3c. The data in FIG. 3c suggests that the ET no D products may be efficiently activated in the radial direction during their axial transmission through Q2, giving rise to improved ETD yield as well as an increase in the extent of structural information which may be identified in the subsequent mass spectrographic analysis.

Since additional activation time may not be required for the transmission-mode method, the overall duty cycle of the apparatus may be unaffected by the radial activation of the electron transfer survivor ions. Consistent with observations from CID of the un-dissociated products from electron transfer and electron capture, increased contributions of the odd-electron c-type ions and the even-electron z-type ions are present in FIG. 3c relative to the results in FIG. 3a, which shows substantial formation of even-electron c- and odd-electron z-ions.

Radial activation for transmission-mode electron transfer ion/ion reactions may also be applied to peptides with PTMs. FIG. 4a shows cation transmission mode electron transfer ion/ion reaction data of a triply-protonated phosphopeptide (DLDVPI PGRFDRRVpSVAAE). A limited degree of ETD was observed, with the presence of 9 out of 32 possible fragments due to N—Cα backbone cleavages. When a dipolar AC voltage (68.93 kHz, 900 $mV_{p-p}$) was applied to Q2 to activate the 2+ species of the peptide ions during the transmission-mode ion/ion reactions, 19 c- and z-ions were obtained, as shown in the data of FIG. 4b. The ETD yield was also improved from 33% to 45%. Under the activation conditions used to collect the spectrum of FIG. 4b, little loss of $H_3PO_4$ from the peptide ions or from the c- and z-sequence ions was observed, suggesting preservation of the PTM sites on the peptide backbone.

Multiply-protonated protein ions may show charge-state-dependent fragmentation in both ETD and ECD experiments. For the lower-charge states of protein ions, the ETD or ECD fragmentation efficiencies appear to be significantly reduced, which may be attributed to non-covalent interactions preventing covalent bond cleavage products from separating. FIG. 5a, for example, shows ETD data derived from the $[M+7H]^{7+}$ ions of ubiquitin subject to cation transmission mode ion/ion reactions. The fragmentation efficiency and number of sequence ions reflected in FIG. 5a are limited. FIG. 5b shows the ETD data collected under the same conditions as that in FIG. 5a, but with application of a dipolar AC voltage (52.06 kHz, 500 $mV_{p-p}$) to Q2, which was in resonance with 6+ charge state of ubiquitin. In FIG. 5b, a total of 46 c- and z-type of sequence ions are observed, compared to 9 observed in FIG. 5a. Accompanying the increase of the ETD products is a more than ten-fold decrease in the signal of the 6+ charge state of ubiquitin ions after radial activation. This observation suggests that most of the 6+ ion population may be comprised of the intact electron transfer products ($[M+7H]^{6+}$), rather than the proton transfer product ($[M+6H]^{6+}$). Upon radial activation of the charge reduced species, the % ETD increases from 9% to 53%. The radial excitation of the 6+ charge state of the ubiquitin ions appears to have reduced sequential ion/ion reactions to some extent. The abundances of 5+ and 4+ charge states of ubiquitin ions decreased roughly two-fold. This may be due to the conversion of the 6+ ions into dissociation products and to a decrease in the ion/ion reaction rate of the 6+ species due to radial excitation, a phenomenon which may be termed "ion parking".

Therefore, by applying radial activation to the first generation intact electron transfer products, more ETD products may be produced and sequential charge reduction ion/ion reactions may be limited to some extent.

Radial activation may therefore be applied to ET no D products during cation transmission-mode electron transfer ion/ion reactions in the collision cell (Q2) of a QqTOF system. The method, in which ion/ion reactions and collisional activation of first generation products occur contemporaneously, may avoid a reduction in duty cycle that would result when the ion/ion reaction and the collisional activation events are separated in time. The activation method uses a relatively high neutral gas pressure in Q2, so that the ions have sufficient axial transit time to be efficiently activated.

The effectiveness of the radial activation for transmission-mode electron transfer ion/ion reactions has thus been demonstrated herein with a doubly protonated tryptic peptide, a triply protonated phosphopeptide and $[M+7H]^{7+}$ ubiquitin ions, where a dipolar AC voltage was applied to Q2 in resonance with the first generation charge-reduced species. A significant increase in the ETD yield and the extent of structural information was observed. Only a small contribution from dissociation of the proton transfer products or loss of the PTM (e.g., phosphoric acid) was observed to result from the application of an activation electric field with a frequency and amplitude selected so as to dissociate electron transfer products. The above experimental examples suggest that radial activation is compatible with cation transmission-mode electron transfer ion/ion reactions and can improve the ETD performance for the relatively-low-charge-state ions of peptides and proteins. While the activation method was demonstrated with a QqTOF system, the method can be used on any type of apparatus that employs a quadrupole collision cell and a mass analyzer.

Since the activation of a particular intact electron transfer product depends on the application of an electric field of suitable amplitude and of a frequency that is a resonant frequency of the ionic species, the frequency applied may be a plurality of frequencies that are either selected to be the known resonant frequencies of ionic products, or may be a band of resonant frequencies that encompass a mass-to-charge (m/z) range. The excitation amplitudes may also be varied correspondingly. As such, ET no D ionic species may be activated using a broadband (that is, multifrequency) AC waveform applied to a pair of quadrupole rods in Q2 during the period of cation transmission/ETD reagent anion storage and transmission mode ion/ion reaction. The approach was demonstrated by activating the intact electron transfer (ET no D) products formed in cation transmission-mode ion/ion reactions of a series of tryptic peptide cations with and without PTMs (phosphorylation and glycosylation) in reaction with azobenzene radical anions in the Q2 LIT. This activation approach may be suitable for tryptic peptide analyses by ETD MS/MS coupled with liquid chromatography (LC). In such an arrangement tryptic peptides would be separated chromatographically and then subjected to MS/MS using ETD in an on-line fashion.

The general operation of the apparatus was very similar to the situation described previously for the first group of experimental results, and thus only differences in the method of operation and the experimental results are described herein.

Horse skeletal muscle myoglobin, bovine cytochrome c, bovine α-casein, lectin from *Erythrina cristagalli* (Cockspur Coral Tree), TPCK-treated trypsin, ammonium bicarbonate and azobenzene were purchased from Sigma-Aldrich (St. Louis, Mo.). Methanol, acetonitrile and glacial acetic acid were obtained from Mallinckrodt (Phillipsburg, N.J.). Trifluoroacetic acid (TFA) was purchased from Pierce (Rockford, Ill.). All materials were used without further purification.

Tryptic digestion was performed on myoglobin and cytochrome c (~1 mg) and followed by reverse-phase high-performance liquid chromatography (HPLC) separation. The fractions were dried in vacuum and then dissolved in 200 μL of 49.5/49.5/1 (v/v/v) methanol/water/acetic acid. *Erythrina cristagalli* lectin and α-casein were also trypsin digested, and then separated by reverse-phase HPLC using a similar procedure.

Figure 6:
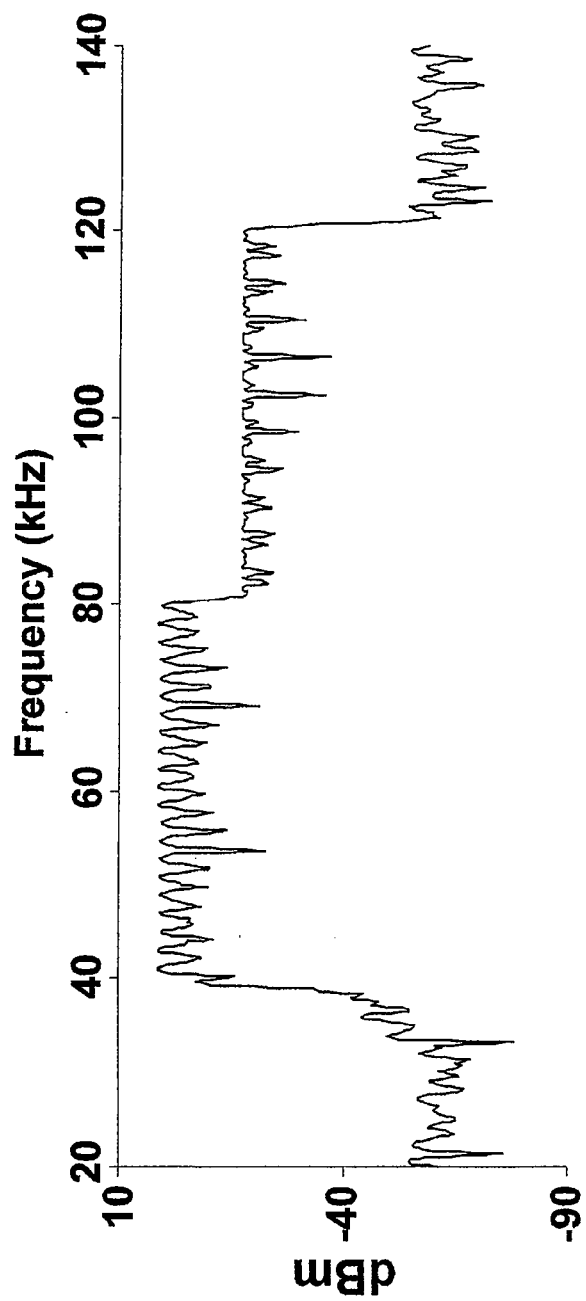
FIG. 6 illustrates the amplitude variation of the broadband frequency spectrum of the dipolar AC voltage applied to a pair of rods of Q2.

A broadband AC waveform produced by the waveform generator (WG) was used as the dipolar AC source, and applied similarly to that described in the first set of examples. Instead of a single AC frequency, the waveform was characterized in frequency bands, each having a starting frequency, ending frequency, frequency spacing, a phase and relative amplitude. The waveform was synthesized in a program, SxWave, provided by MDS SCIEX; an example waveform is shown in FIG. 6. The salient parameters summarized in Table 1, where the relative voltage amplitude shown. The waveforms were downloaded to the waveform generator. In operation, the broadband AC voltage excitation of the pair of quadrupole elements of Q2 was maintained for the time period of the transmission-mode electron transfer ion/ion reaction.

TABLE 1

Frequency band characteristics

| Band | $Freq_{first}$ (kHz) | $Freq_{last}$ (kHz) | $Freq_{inc}$ (kHz) | Phase | Amplitude |
|---|---|---|---|---|---|
| 1 | 40 | 80 | 0.5 | quadratic | 1.0 |
| 2 | 80.5 | 120.5 | 1.0 | quadratic | 0.3 |

The frequency bands of the broadband waveform of Table 1 and FIG. 6 were determined as follows:

The mass range excited in Band 1 was set to m/z=950-1900 in order to activate the first generation intact ET products within this particular mass-to-charge (m/z) range since the majority of tryptic peptide ions contain 9-17 amino acid residues (approximate average residue mass=112 Da), with a charge state of +2 being dominant upon ESI. Additionally, when one or two trypsin-missed cleavages are taken into account, the sizes of the resulting peptides may increase considerably, usually giving rise to dominant high charge states of +3 upon ESI, with first generation intact ET products thereof (doubly charged) also falling into this m/z range.

The mass range activated in Band 2 was set to m/z=475-950 in order to enhance ETD performance of the precursor ions (the minority of tryptic peptides containing 5-8 amino acid residues) with their first generation intact ET products falling into this m/z region. A lower AC voltage value is applied in Band 2 so as to minimize the ejection of directly-produced ETD fragments, which may be formed with precursor ions of low mass-to-charge ratio.

A broadband waveform such as that of Table 1 may be expected to enhance the ETD result for relatively high m/z ions for the majority of tryptic peptides, which may be suitable for activating the first generation ET no D products without apparently losing the structural information derived from normal ETD.

Band 1, 40-80 kHz, corresponds to m/z=950-1900 when the low-mass-cut-off (LMCO) of Q2 LIT in the reaction/activation step is set to m/z=170 and the frequency spacing of the band is set to 0.5 kHz. Band 2, 80.5-120.5 kHz, corresponds to the m/z=475-950 with the same LMCO, and the frequency spacing of this band is set to 1 kHz. Collisional activation performance during the ion/ion reaction was found to be insensitive to frequency spacing when the spacing was 1 kHz or less.

The temporal waveform may be determined by an inverse Fourier transform of the desired frequency spectral content, and the peak-to-average value of the AC voltage may be controlled by choosing a particular spectral phase function. In this example, a quadratic spectral phase variation is used, a description of which may be found in the background section of U.S. Pat. No. 5,324,939 to Louris et al.

Different voltage amplitude ratios of the two frequency bands were investigated. When the relative amplitude for the Band 2 was low (e.g., ratios of 1/0 and 1/0.2), no enhancement for the ETD performance of +2 peptide ions falling within the second category was observed with a dipolar AC voltage of $3.0 V_{p-p}$ or $3.5 V_{p-p}$. With increased voltage amplitude for the Band 2 (e.g., ratios between 1/0.3 and 1/1), and a Band 1 voltage value less than $3.0 V_{p-p}$ or $3.5 V_{p-p}$, substantially the same improvement in the extent of sequence information from activation of ET no D+2 peptide ions falling into the second category was found. Higher voltage amplitudes applied to this region significantly decreased the ion/ion reaction rate. This may be attributed to a phenomenon referred to as ion parking, which reduced the reaction efficiency. Increased amplitude for the low mass region also produced more CID fragments from the precursor ions. Therefore, a relative amplitude ratio of the two bands of about 1/0.3 and a waveform generator output of about $3.0 V_{p-p}$ were determined, in this study, to be the most effective parametric values in the present apparatus for the activation of ET no D products, resulting in informative c-/z-type species, with minimal CID fragment ions from the precursor ion or proton transfer products.

Figure 7:
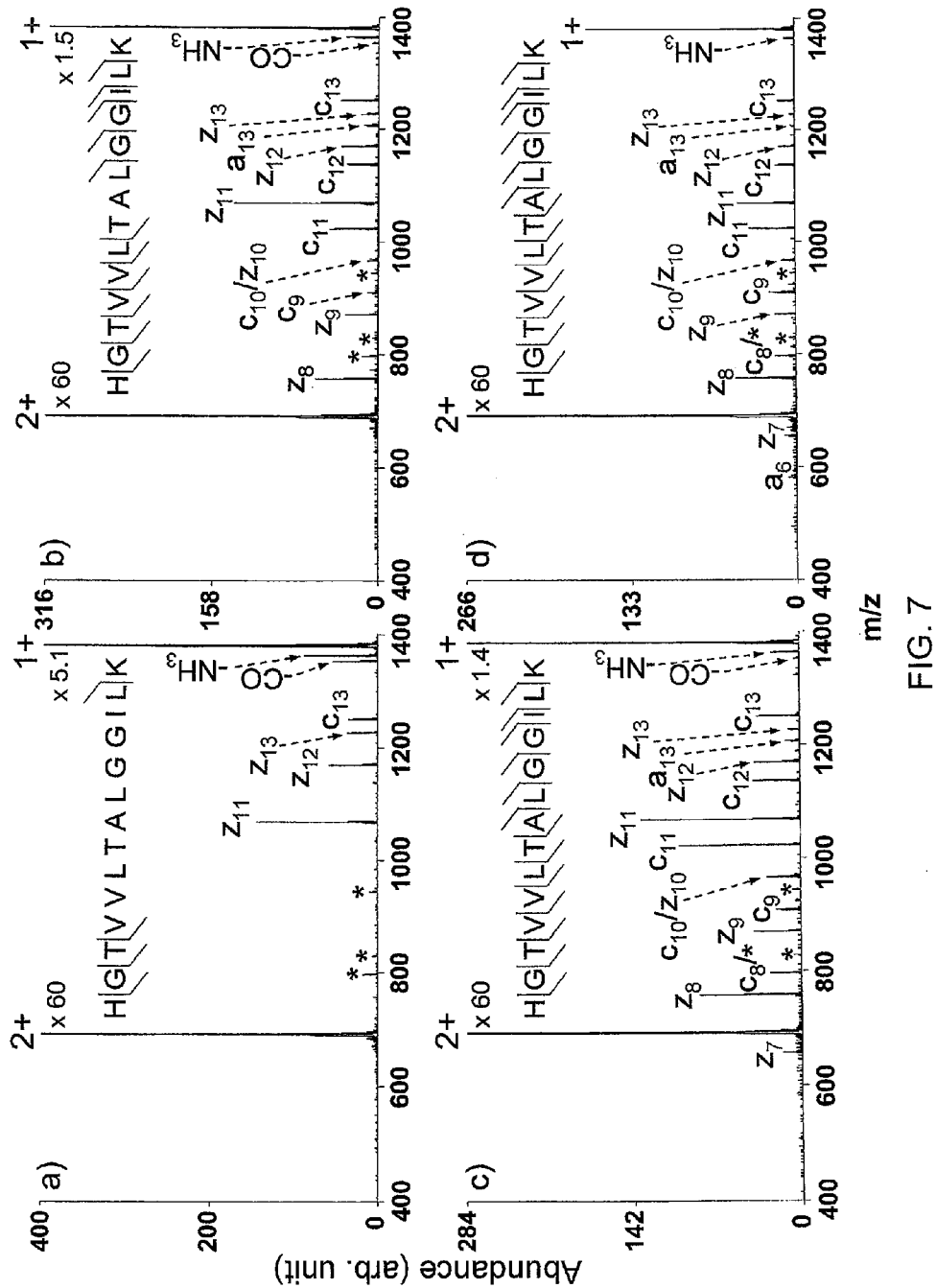
FIG. 7 illustrates the spectra of electron transfer ion/ion reactions of doubly charged tryptic peptide HGTVVLTALG-GILK from myoglobin with azobenzene radical anions (a) with no activation; (b) with multi-frequency activation, an amplitude of 2.8 $V_{p-p}$; (c) with multi-frequency activation, an amplitude of 3.0 $V_{p-p}$; and, (d) with broadband waveform activation, an amplitude of 3.2 $V_{p-p}$. (The peaks labeled with asterisks are present during the isolation)

For the majority of the tryptic peptides, with first generation intact electron transfer (ET no D) product ions falling into the m/z=950-1900 range, the optimal dipolar AC amplitude was found to be $3.0 V_{p-p}$, as illustrated in FIG. 7. The sequence coverage for doubly protonated HGTVVLTALG-GILK, defined as the percentage of possible N—$C_\alpha$ cleavages, was 31% with no activation (FIG. 7a); 85% with an output of $2.8 V_{p-p}$ (FIG. 7b); 100% with an output of $3.0 V_{p-p}$ (FIG. 7c); and, 100% with an output of $3.2 V_{p-p}$ (FIG. 7d).

Even though full sequence coverage appeared to have been obtained with both $3.0 V_{p-p}$ and $3.2 V_{p-p}$ outputs, the abundances of the fragments was lower with the higher amplitude voltage (FIG. 7d), and this result may be due to ion ejection or CID of the first generation products. Similar experiments performed on other tryptic peptides, with and without PTMs (phosphorylation and glycosylation), also showed that the approximately $3.0 V_{p-p}$ AC voltage amplitude may be suitable for activation during the transmission mode ETD process using the waveform of Table 1. This corresponds to 213 $mV_{p-p}$ per frequency component over the 40-80 kHz range, and 64 $mV_{p-p}$ per frequency component over the 80.5-120.5 kHz range.

Most of the tryptic peptides are appear to be doubly charged after ESI, with singly charged intact ET products falling within the low frequency band, the results shown in FIG. 7 are relevant to the most common scenario.

Figure 8:
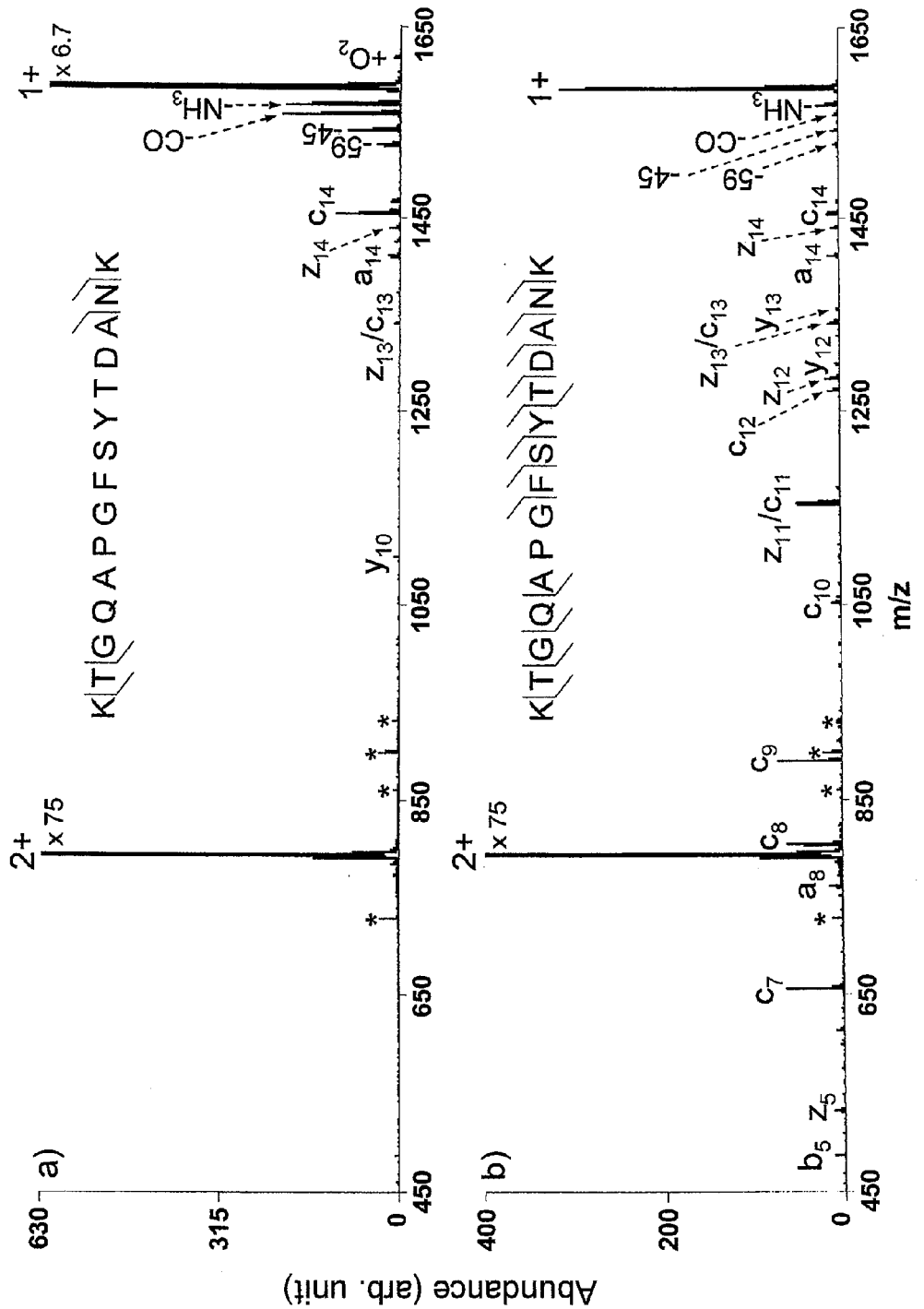
FIG. 8 illustrates the spectra of doubly charged tryptic peptide KTGQAPGFSYTDANK from cytochrome c with azobenzene radical anions (a) without activation; and, (b) with activation via the broadband waveform. (The peaks labeled with asterisks are present after isolation in the absence of ion/ion reaction and application of the waveform)

FIG. 8 shows experimental results for doubly-protonated KTGQAPGFSYTDANK, using the multi-frequency waveform with an output of $3.0 V_{p-p}$. Broadband activation provides 86% of the sequence coverage (FIG. 8b) compared to only 29% derived from normal ETD (FIG. 8a), with a few fragments formed from CID of the proton transfer product. Comparing FIGS. 8a and 8b, the abundances of the peaks observed in the ETD spectrum of m/z=950 and greater dropped a minor amount upon activation with the $3.0 V_{p-p}$ waveform, but are still sufficiently abundant to be used for sequencing. The product ion $a_8$ may be a radical species, which may be generated from a minor cleavage channel in ETD. Even-electron fragment ions $y_{12}$ and $y_{13}$, observed in FIG. 8b, may arise either from CID of the proton transfer product or from a minor cleavage channel in ETD.

Figure 9:
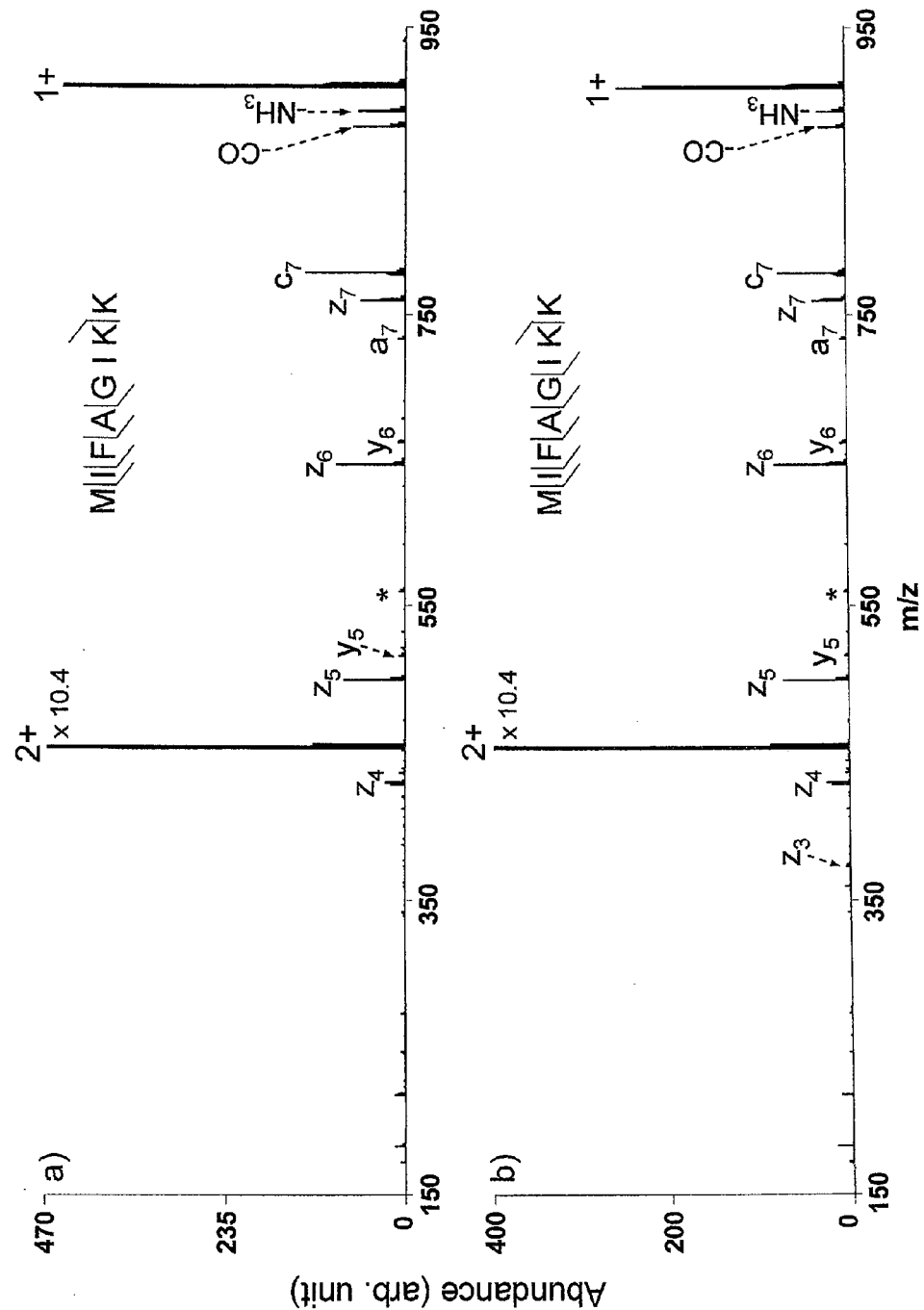
FIG. 9 illustrates spectra of doubly-charged tryptic peptide MIFAGIKK from cytochrome c with azobenzene radical anions (a) without activation; (b) with activation via the broadband waveform. (The peaks labeled with asterisks are present during the isolation)

FIG. 9 shows an example of data typical for the minority of doubly-protonated tryptic peptides that generate first-generation intact electron transfer product ions that fall into the higher frequency activation band of the waveform (m/z=475-950). Eighty-six percent sequence coverage was obtained from ETD of the doubly-charged peptide MIFAGIKK with broad-band activation with a $3.0 V_{p-p}$ output (FIG. 9b), compared to 71% coverage in the absence of activation by the broadband waveform (FIG. 9a). Sequence coverage tends to be high for peptides of this type without broadband waveform activation. Improvements in sequence coverage arising from the use of the broadband waveform may thus be more limited. Nevertheless, improved sequence coverage was generally observed in cases in which the sequence coverage is not already 100%, provided the amplitude of the waveform is sufficiently low to avoid ejecting the product ions formed directly from ETD.

Figure 10:
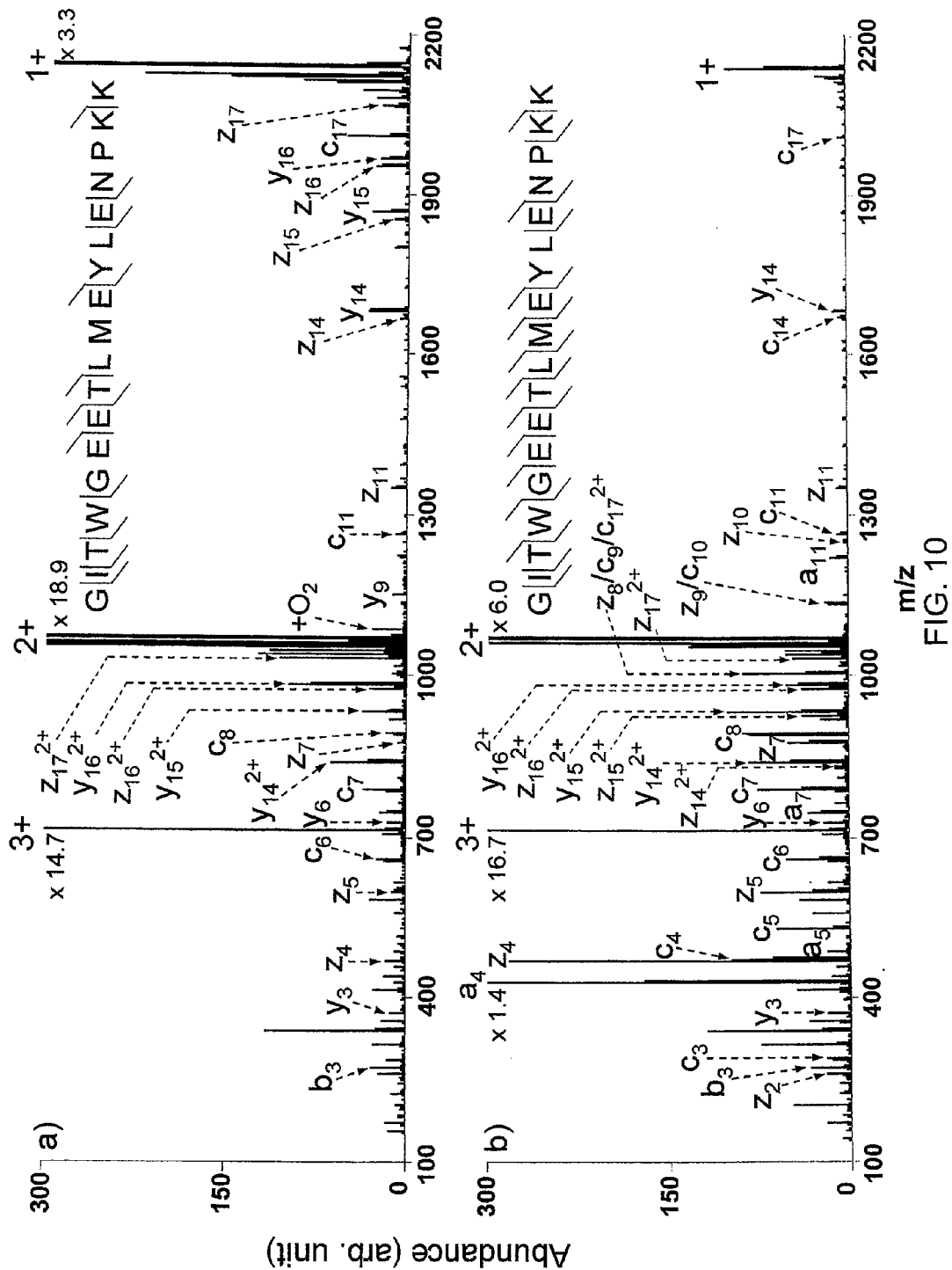
FIG. 10 illustrates the spectra of triply-charged tryptic peptide GITWGEETLMEYLENPKK from bovine cytochrome c with azobenzene radical anions with (a) no activation; and, (b) activation using the broadband waveform.

Although most of the tryptic peptides are doubly charged upon ESI, a significant fraction of the tryptic peptides are of a higher charge state. For triply-charged tryptic peptides, either the first generation intact electron transfer product, which is doubly charged, falls within the m/z=950-1900 range; or, the doubly charged intact electron transfer product falls within the m/z=475-950 range while the singly charged intact electron transfer product, formed by sequential electron transfer, falls within the m/z=950-1900 range. An example that applies to the first situation is shown in FIG. 10.

The sequence coverage for the peptide GITWGEETLM-EYLENPKK from bovine cytochrome c increased from 65% (13 out of 34 possible c- and z-type fragments) to 88% (23 out of 34 possible c- and z-type fragments) upon multi-frequency collisional activation during the ion/ion reaction. Compared to the ETD spectrum obtained without the broadband waveform in FIG. 10a, a few radical a-type species, $a_4$, $a_5$, $a_7$ and $a_{11}$, were observed in the activated ETD spectrum, as shown in FIG. 10b, which may arise from minor ETD cleavage channels. The $a_4$ product ion, which may be due to the $C_\alpha$—CO cleavage between tryptophan and glycine residues, was observed to be the most abundant fragment generated upon activation. The abundances of, and the number of, fragments in the low m/z range increased significantly, but the abundances, and the number of, the fragments in the high m/z range decreased. This may be due to simultaneous activation of the fragments generated from the normal ETD process. The diagnostic information gained, however, may more than compensate for that lost. This result appears to be consistent with the experimental results from other triply-charged tryptic peptides for which the first scenario applies (data not shown). The abundance of +1 species decreased roughly six-fold, which may result from dissociation of the +2 ET no D product as well as reduction of the ion/ion reaction rate of the +2 species due to the ion acceleration.

By applying broadband activation to precursor ions with first generation ET products falling into a defined m/z range, more sequence information can be produced and sequential charge reduction reactions can be limited to some extent.

For the second scenario mentioned above, high (frequently full) sequence coverage is usually obtained. In this circumstance, there may be no apparent advantage in using a broadband waveform. However, applying the broadband waveform to all precursor ions would minimize tuning the dipolar AC voltage frequency from one analyte ion to the next.

Figure 11:
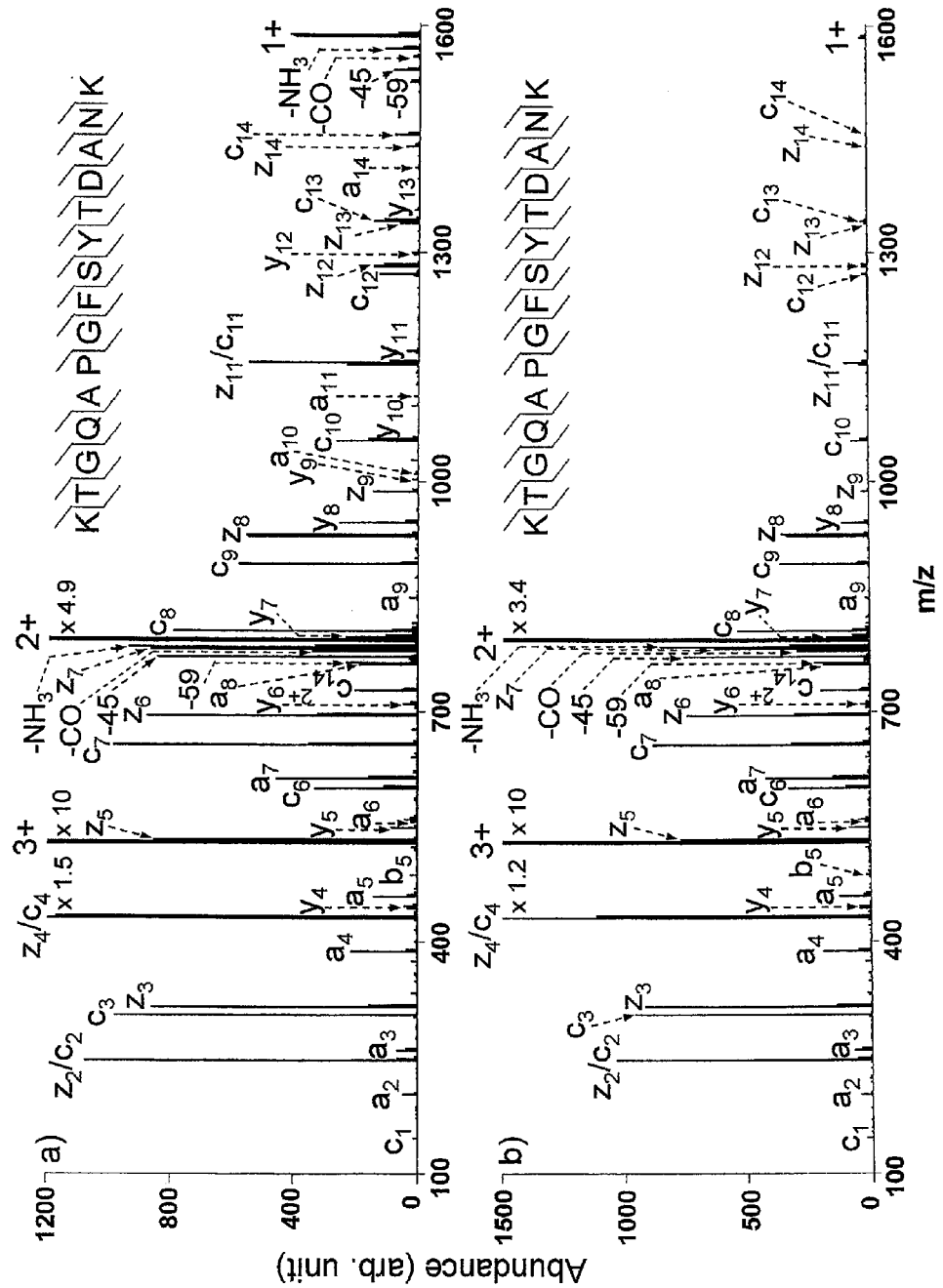
FIG. 11 illustrates spectra of triply-charged tryptic peptide KTGQAPGFSYTDANK from bovine cytochrome c with azobenzene radical anions (a) without activation; and, (b) with activation using the broadband waveform.

FIG. 11 shows ETD results for the triply charged peptide KTGQAPGFSYTDANK from bovine cytochrome c without (FIG. 11a) and with (FIG. 11b) multi-frequency activation. The same sequence coverage was derived from both spectra, which suggest that there may not be a loss of the sequence information under activation using a dipolar AC voltage of 3.0 $V_{p-p}$. Other peptides having similar characteristics gave similar results (data not shown), showing that almost the same sequence information may obtained without or with activation during electron transfer ion/ion reactions for peptide ions that fall into this category.

Figure 12:
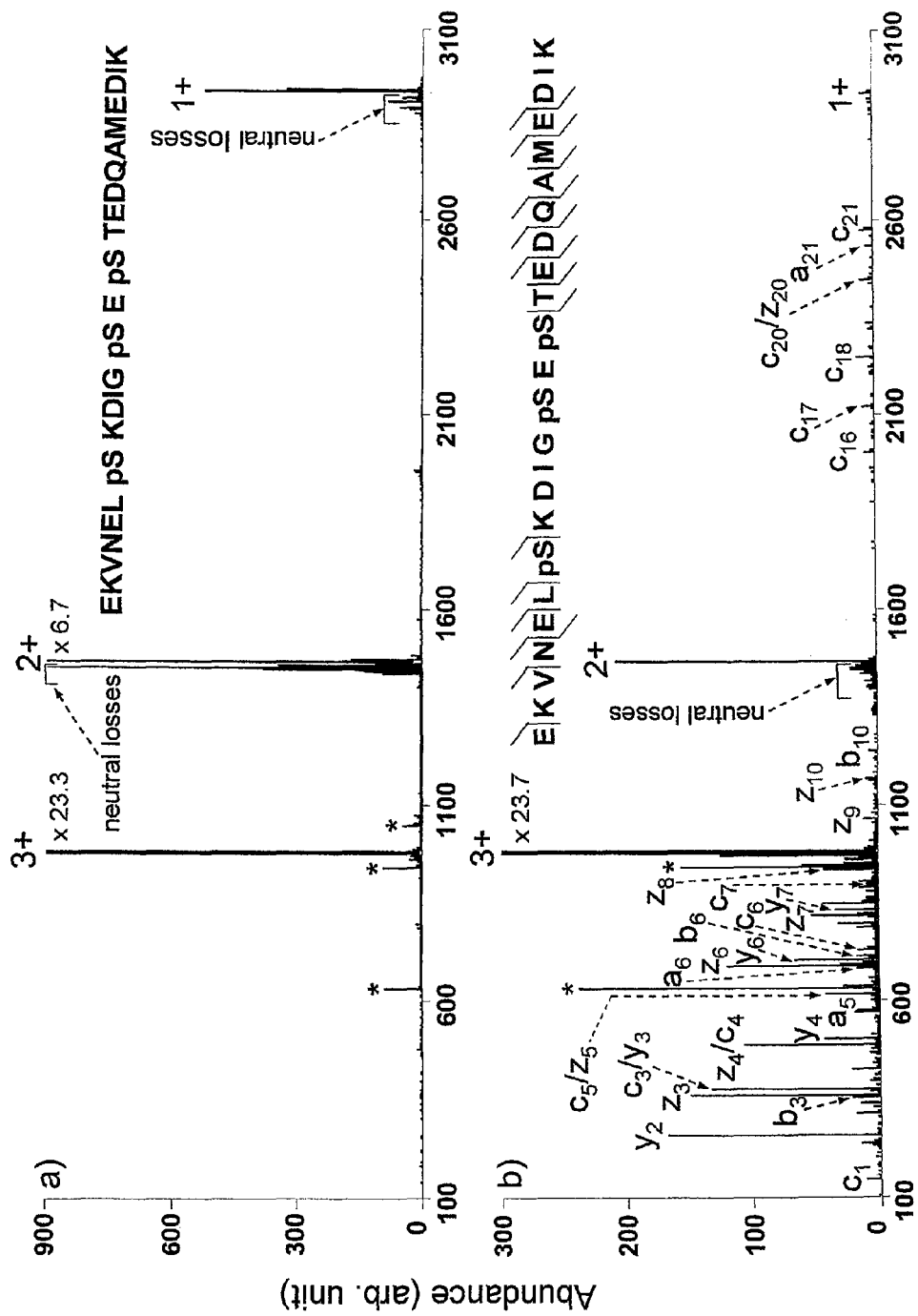
FIG. 12 illustrates spectra of triply charged tryptic phosphopeptide EKVNELpSKDIGpSEpSTEDQAMEDIK from α-casein with azobenzene radical anions (a) without activation; and, (b) with activation using the broadband waveform. (The peaks labeled with asterisks are present during the isolation)
Figure 13:
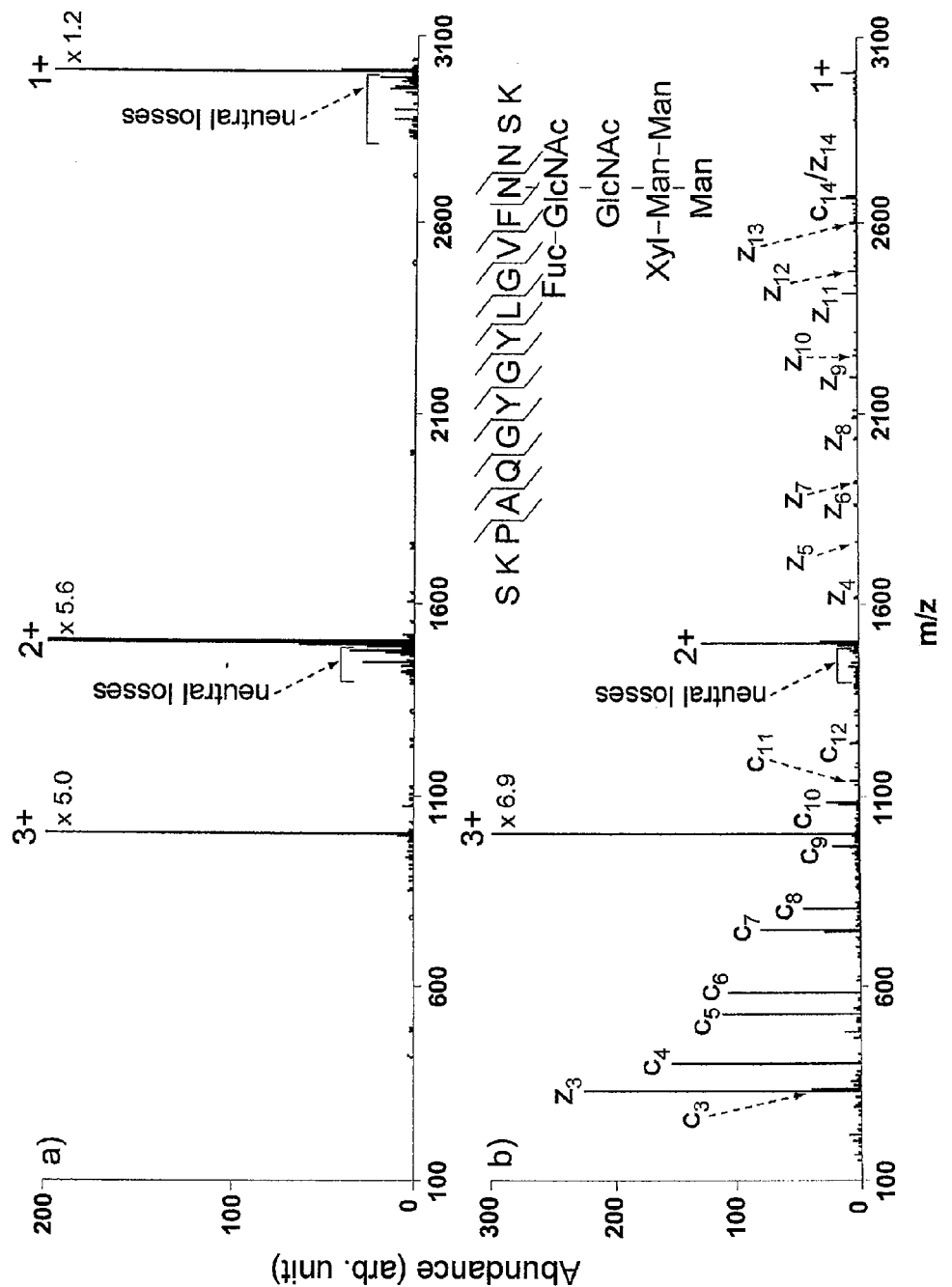
FIG. 13 illustrates the spectra of triply-charged tryptic glycopeptide SKPAQGYGYLGVFgNNSK from *Erythrina cristagalli* lectin with azobenzene radical anions (a) without activation; and, (b) with activation using the broadband waveform.

Collisional activation using the broadband waveform with a 3.0 $V_{p-p}$ output was also performed to examine the effect on tryptic peptides with phosphorylation. ETD and ECD are particularly useful for determining the sites of labile post-translational modifications as, unlike CID, cleavage of backbone bonds is favored over cleavage of the modification. The waveform of Table 1 was applied to several modified peptide ions. FIG. 12 shows transmission mode ETD spectra of triply protonated EKVNELpSKDIGpSEpSTEDQAMEDIK from α-casein with no activation (FIG. 12a) and with activation (FIG. 12b). For this particular peptide, no sequence information was obtained without multi-frequency activation. However, under the activation conditions, 61% of the sequence is observed in the c- and z-type ions, with one phosphorylation site identified to be the seventh residue from the N-terminus. The other two phosphorylations sites do not appear to be localizable to specific residues. In addition to the c- and z-type ions produced, some a-, b- and y-type species were also formed, which may have arisen either from the minor ETD channels or from CID of even-electron species. The loss of phosphoric acid ($H_3PO_4$), commonly seen in CID spectra of phosphopeptides, did not appear to be observed in the activated ETD spectrum shown in FIG. 12b. The 3.0 $V_{p-p}$ output of the waveform generator may be high enough to dissociate the electron transfer survivor ions, but not high enough to cleave the covalent bonds of the even-electron species to a significant extent.

A tryptic peptide with one N-linked glycosylation site (see inset of FIG. 13b) was activated using the broadband waveform with an output of 3.0 $V_{p-p}$. This N-linked glycopeptide, SKPAQGYGYLGVFgNNSK from *Erythrina cristagalli* lectin, had been extensively studied previously by ECD and infrared multiphoton dissociation (IRMPD) in an FT-ICR instrument, and ETD and CID in a linear ion trap, with ECD and ETD providing peptide sequence and the IRMPD and CID providing information about the glycan structure. Although no sequence information was generated from electron transfer to the triply charged glycopeptide (FIG. 13a), the glycosylation site was localized to be the fourth amino acid from the C-terminus using the m/z difference between the fragments $z_3$ and $z_4$ upon activation. The use of the broadband waveform in conjunction with the transmission mode ion/ion reaction resulted in the generation of fragments from 75% of the possible N—$C_\alpha$ bond cleavages (FIG. 13b). Furthermore, with the broadband activation, there did not appear to be evidence for cleavages of the glycosidic bonds, suggesting a minimal contribution from CID at this dipolar AC waveform amplitude. However, some relatively abundant peaks due to cleavages of glycosidic bonds were noted when the amplitude increased to 3.1 $V_{p-p}$ (data not shown).

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein as being necessary, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A method of analyzing molecules, the method comprising:
   providing a linear ion trap (LIT);
   injecting a first population of ions into the ion trapping volume so that the first population is stored in a trapping volume between a pair of end caps;
   injecting a second population of ions into the ion trapping volume such that at least a partial physical overlap of the first and the second ion populations occurs;
   producing ionic products by applying an AC electric field to the LIT transverse to a direction of motion of either the first ionic population or the second ionic population caused by application of a DC electric field between the pair of end caps; and
   performing mass spectrometry on ionic products ejected from the LIT.

2. The method of claim 1, wherein the step of mass spectrometry is performed by operating a second LIT in a mass-selective axial ejection (MSAE) mode.

3. The method of claim 1, wherein the step of mass spectrometry is performed by a time-of-flight mass analyzer.

4. The method of claim 1, wherein the step of mass spectrometry is performed by a reflectron-type mass spectrometer.

5. The method of claim 1, wherein the first population of ions are anions and the second population of ions are anions.

6. The method of claim 1, wherein the first population of ions are cations and the second population of ions are anions.

7. The method of claim 1, wherein the step of producing ion products includes selecting a frequency of the AC electric field so as to activate a specific ionic species.

8. The method of claim 7, wherein the selected frequency is a resonant frequency of the specific ionic species.

9. The method of claim 7, wherein the ionic species to be activated are within a selected mass-to-charge-range.

10. The method of claim 1, wherein the step of producing ionic products includes applying an electric field along an axis of injection of the ions so as to eject the ionic products into the mass spectrometer.

11. The method of claim 1, wherein the step of injecting the first ion population includes the step of selecting an ion type from a plurality of ion types prior to injection into the ion trap.

12. The method of claim 1, wherein the step of injecting the second ion population includes the step of selecting an ion type from a plurality of ion types prior to injection into the ion trap.

13. The method of claim 1, wherein a frequency of the AC electric field is selected to be the resonant frequency of at least one reaction product between the first and the second ion populations.

14. The method of claim 13, wherein a pressure of a neutral gas in the ion trap is about 5 mTorr.

15. The method of claim 14, wherein the neutral gas is nitrogen.

16. The method of claim 1, wherein the step of producing ionic products is performed by applying an AC voltage between a pair of axially-symmetrical quadrupole rods of the LIT.

17. The method of claim 1, wherein at least one of the first ion population or second ion population is produced by an electrospray ionization (ESI) device.

18. The method of claim 1, wherein at least one of the first ion population or second ion population is produced by an atmosphere pressure chemical ionization (APCI) needle.

19. The method of claim 1, wherein the first and the second ion populations are injected along an axis parallel to the rods in the LIT.

20. The method of claim 19, wherein the step of producing ionic products includes applying an AC voltage to a pair of rods symmetrical about the axis parallel to the rods.

21. The method of claim 20, wherein the step of producing ionic products includes the step of ejecting ionic products by applying an electric field parallel to the axis parallel to the rods.

22. The method of claim 19, wherein one of the first or the second population of ions comprises a multiply charged ion, and the other of the first or the second population of ions comprises a singly charged ion that will engage in electron transfer with the multiply charged ion.

23. The method of claim 1, wherein the AC electric field is applied to an opposing pair of rods of the LIT.

* * * * *

UNITED STATES PATENT AND TRADEMARK OFFICE
CERTIFICATE OF CORRECTION

PATENT NO.       : 8,598,517 B2  
APPLICATION NO.  : 12/809280  
DATED            : December 3, 2013  
INVENTOR(S)      : Scott A. McLuckey et al.

Page 1 of 1

It is certified that error appears in the above-identified patent and that said Letters Patent is hereby corrected as shown below:

On the Title Page

Left column, item (87), after "PCT Pub. Date:" replace "Dec. 17, 2008" with --July 9, 2009--.

Signed and Sealed this
Twenty-seventh Day of May, 2014

Michelle K. Lee
*Deputy Director of the United States Patent and Trademark Office*